US00RE41956E

(19) United States
(12) Reissued Patent
Klitgaard et al.

(10) Patent Number: US RE41,956 E
(45) Date of Reissued Patent: *Nov. 23, 2010

(54) DOSE SETTING LIMITER

(75) Inventors: Peter Christian Klitgaard, Glostrup (DK); Steffen Hansen, Hillerod (DK); Bo Radmer, Hillerod (DK); Claus Schmidt Moller, Fredensborg (DK)

(73) Assignee: Novo Nordisk A/S, Bagsvaerd (DK)

( * ) Notice: This patent is subject to a terminal disclaimer.

(21) Appl. No.: 11/122,211

(22) Filed: May 4, 2005

Related U.S. Patent Documents

Reissue of:
(64) Patent No.: 6,582,404
Issued: Jun. 24, 2003
Appl. No.: 09/655,922
Filed: Sep. 6, 2000

U.S. Applications:
(60) Provisional application No. 60/155,612, filed on Sep. 23, 1999.

(30) Foreign Application Priority Data

Sep. 16, 1999 (DK) ..... 1999 01309

(51) Int. Cl.
*A61M 5/00* (2006.01)
*A61M 5/178* (2006.01)
*A61M 5/315* (2006.01)

(52) U.S. Cl. ..... 604/181; 604/186; 604/207; 604/208; 604/211; 604/224

(58) Field of Classification Search ..... 604/181, 604/186, 187, 207–208, 211, 224
See application file for complete search history.

(56) References Cited

U.S. PATENT DOCUMENTS 4,470,317 A 9/1984 Sabloewski et al.

(Continued)

FOREIGN PATENT DOCUMENTS

DE 36 09 555 9/1987

(Continued)

OTHER PUBLICATIONS

U.S. Appl. No. 10/442,855 File History on Feb. 8, 2008.

(Continued)

*Primary Examiner*—Kevin C Sirmons
*Assistant Examiner*—Andrew M Gilbert
(74) *Attorney, Agent, or Firm*—Marc A. Began

(57) ABSTRACT

A limiting mechanism which prevents the setting of a dose, which exceeds the amount of liquid left in a cartridge of an injection device, is disclosed. The injection device is the type where a dose is set by rotating a dose setting member relative to a driver and away from a fixed stop in the injection device. The dose setting member interfaces the driver such that the dose setting member can be rotated in one direction without rotating the driver. The dose is injected by rotating back the dose setting member which during the backward rotation carries the driver with it. Rotating the driver causes the piston rod to move forward inside the cartridge and expel some of the liquid contained in the cartridge. The driver is provided with a track having a length which is related to the total amount of liquid in the cartridge and which track is engaged by a track follower coupled to the dose setting member to follow rotation of this dose setting member. Each time a dose is set and injected, the track follower moves further into the track. When the track follower reaches the end of the track the dose setting member can not be rotated further, and a dose larger than the remaining liquid in the cartridge cannot be set.

19 Claims, 2 Drawing Sheets

U.S. PATENT DOCUMENTS

| | | | | |
|---|---|---|---|---|
| 4,498,904 | A | | 2/1985 | Turner et al. |
| 4,568,335 | A | | 2/1986 | Updike et al. |
| 4,585,439 | A | | 4/1986 | Michel |
| 4,833,379 | A | | 5/1989 | Kaibel et al. |
| 4,865,591 | A | | 9/1989 | Sams |
| 4,883,472 | A | | 11/1989 | Michel |
| 4,919,596 | A | | 4/1990 | Slate et al. |
| 4,936,833 | A | | 6/1990 | Sams |
| 4,973,318 | A | * | 11/1990 | Holm et al. |
| 4,994,033 | A | | 2/1991 | Shockey et al. |
| 5,112,317 | A | | 5/1992 | Michel |
| 5,207,752 | A | | 5/1993 | Sorenson et al. |
| 5,226,895 | A | * | 7/1993 | Harris ..... 604/208 |
| 5,246,417 | A | | 9/1993 | Haak et al. |
| 5,257,987 | A | | 11/1993 | Athayde et al. |
| 5,271,527 | A | | 12/1993 | Haber et al. |
| 5,279,585 | A | | 1/1994 | Balkwill |
| 5,279,586 | A | | 1/1994 | Balkwill |
| 5,281,198 | A | | 1/1994 | Haber et al. |
| 5,284,480 | A | | 2/1994 | Porter et al. |
| 5,304,152 | A | | 4/1994 | Sams |
| 5,308,340 | A | | 5/1994 | Harris |
| 5,314,412 | A | | 5/1994 | Rex |
| 5,318,540 | A | | 6/1994 | Athayde et al. |
| 5,320,609 | A | | 6/1994 | Haber et al. |
| 5,331,954 | A | | 7/1994 | Rex et al. |
| 5,370,629 | A | | 12/1994 | Michel et al. |
| 5,383,865 | A | | 1/1995 | Michel |
| 5,440,976 | A | | 8/1995 | Giuliano et al. |
| 5,445,606 | A | | 8/1995 | Haak et al. |
| 5,447,150 | A | | 9/1995 | Bacon |
| 5,478,316 | A | | 12/1995 | Bitdinger et al. |
| 5,480,387 | A | | 1/1996 | Gabriel et al. |
| 5,492,534 | A | | 2/1996 | Athayde et al. |
| 5,505,704 | A | | 4/1996 | Pawelka et al. |
| 5,546,932 | A | | 8/1996 | Galli |
| 5,549,575 | A | | 8/1996 | Giambatista et al. |
| 5,584,815 | A | | 12/1996 | Pawelka et al. |
| 5,591,136 | A | | 1/1997 | Gabriel |
| 5,599,314 | A | | 2/1997 | Neill |
| 5,611,783 | A | | 3/1997 | Mikkelsen |
| 5,626,566 | A | | 5/1997 | Petersen et al. |
| 5,645,052 | A | | 7/1997 | Kersey |
| 5,674,204 | A | | 10/1997 | Chanoch |
| 5,679,111 | A | | 10/1997 | Hertman et al. |
| 5,681,285 | A | | 10/1997 | Ford et al. |
| 5,685,864 | A | | 11/1997 | Shanley et al. |
| 5,688,251 | A | | 11/1997 | Chanoch |
| 5,709,662 | A | | 1/1998 | Olive et al. |
| 5,716,990 | A | | 2/1998 | Bagshawe et al. |
| 5,725,508 | A | | 3/1998 | Chanoch et al. |
| 5,743,889 | A | | 4/1998 | Sams |
| 5,755,692 | A | | 5/1998 | Manicom |
| 5,823,998 | A | | 10/1998 | Yamagata |
| 5,827,232 | A | | 10/1998 | Chanoch ..... 604/208 |
| 5,843,036 | A | | 12/1998 | Olive et al. |
| 5,882,718 | A | | 3/1999 | Pommer et al. |
| 5,898,028 | A | | 4/1999 | Jensen et al. |
| 5,921,966 | A | | 7/1999 | Bendek et al. |
| 5,928,201 | A | | 7/1999 | Poulsen et al. |
| 5,938,642 | A | | 8/1999 | Burroughs et al. |
| 5,947,934 | A | | 9/1999 | Hansen et al. |
| 5,951,530 | A | | 9/1999 | Steengaard et al. |
| 5,954,689 | A | | 9/1999 | Poulsen |
| 5,961,496 | A | | 10/1999 | Nielsen et al. |
| 5,980,491 | A | | 11/1999 | Hansen |
| 5,984,900 | A | | 11/1999 | Mikkelsen |
| 6,003,736 | A | | 12/1999 | Ljunggren |
| 6,004,297 | A | * | 12/1999 | Steenfeldt-Jensen et al. ..... 604/207 |
| 6,010,485 | A | | 1/2000 | Buch-Rasmussen et al. |
| 6,033,376 | A | | 3/2000 | Rockley |
| 6,033,377 | A | | 3/2000 | Rasmussen et al. |
| 6,048,336 | A | | 4/2000 | Gabriel |
| 6,074,372 | A | | 6/2000 | Hansen |
| 6,086,567 | A | | 7/2000 | Kirchhofer et al. |
| 6,096,010 | A | | 8/2000 | Walters |
| 6,110,149 | A | | 8/2000 | Klitgaard et al. |
| 6,129,080 | A | | 10/2000 | Pitcher et al. |
| 6,146,361 | A | | 11/2000 | DiBiasi et al. |
| 6,193,698 | B1 | | 2/2001 | Kirchhofer et al. |
| 6,221,046 | B1 | | 4/2001 | Burroughs et al. |
| 6,221,053 | B1 | | 4/2001 | Walters et al. |
| 6,231,540 | B1 | | 5/2001 | Smedegaard |
| 6,235,004 | B1 | | 5/2001 | Steenfeldt-Jensen et al. |
| 6,248,090 | B1 | | 6/2001 | Jensen et al. |
| 6,248,095 | B1 | | 6/2001 | Giambatistia et al. |
| 6,258,062 | B1 | | 7/2001 | Thielen et al. |
| 6,269,340 | B1 | | 7/2001 | Ford et al. |
| 6,277,097 | B1 | | 8/2001 | Mikkelsen et al. |
| 6,277,098 | B1 | | 8/2001 | Klitmose et al. |
| 6,281,225 | B1 | | 8/2001 | Hearst et al. |
| 6,283,941 | B1 | | 9/2001 | Schoenfeld et al. |
| 6,287,283 | B1 | | 9/2001 | Ljunggreen et al. |
| 6,302,869 | B1 | | 10/2001 | Klitgaard |
| 6,312,413 | B1 | | 11/2001 | Jensen et al. |
| 6,340,357 | B1 | | 1/2002 | Poulsen et al. |
| 6,379,339 | B1 | | 4/2002 | Klitgaard et al. |
| 6,514,230 | B1 | | 2/2003 | Munk et al. |
| 6,547,763 | B2 | | 4/2003 | Steenfeldt-Jensen et al. |
| 6,547,764 | B2 | | 4/2003 | Larsen et al. |
| 6,562,011 | B1 | | 5/2003 | Buch-Rasmussen et al. |
| 6,569,126 | B1 | | 5/2003 | Poulsen et al. |
| 6,582,404 | B1 | | 6/2003 | Klitgaard et al. |
| 6,605,067 | B1 | | 8/2003 | Larsen |
| 6,613,019 | B2 | | 9/2003 | Munk |
| 6,692,472 | B2 | | 2/2004 | Hansen et al. |
| 6,716,198 | B2 | | 4/2004 | Larsen |
| 6,726,661 | B2 | | 4/2004 | Munk et al. |
| 6,770,288 | B2 | | 8/2004 | Duirs |
| 6,796,970 | B1 | | 9/2004 | Klitmose et al. |
| 6,893,415 | B2 | | 5/2005 | Madsen et al. |
| 6,899,699 | B2 | | 5/2005 | Enggaard |
| 6,945,961 | B2 | | 9/2005 | Miller et al. |
| 7,008,399 | B2 | | 3/2006 | Larsen et al. |
| 7,090,662 | B2 | | 8/2006 | Wimpenny et al. |
| 7,094,221 | B2 | | 8/2006 | Veasey et al. |
| 7,104,972 | B2 | | 9/2006 | Moller et al. |
| 7,133,329 | B2 | | 11/2006 | Skyggebjerg et al. |
| 7,175,055 | B2 | | 2/2007 | Hansen et al. |
| 7,241,278 | B2 | | 7/2007 | Moller |
| 2002/0007154 | A1 | | 1/2002 | Hansen et al. |
| 2002/0077852 | A1 | | 6/2002 | Ford et al. |
| 2002/0120235 | A1 | | 8/2002 | Enggaard |
| 2003/0039679 | A1 | | 2/2003 | Duirs |
| 2003/0172924 | A1 | | 9/2003 | Staniforth et al. |
| 2004/0186431 | A1 | | 9/2004 | Graf et al. |
| 2004/0210199 | A1 | | 10/2004 | Atterbury et al. |
| 2004/0236282 | A1 | | 11/2004 | Braithwaite |
| 2004/0249348 | A1 | | 12/2004 | Wimpenny et al. |
| 2004/0260247 | A1 | | 12/2004 | Veasey et al. |
| 2004/0267207 | A1 | | 12/2004 | Veasey et al. |
| 2005/0004529 | A1 | | 1/2005 | Veasey et al. |
| 2005/0019400 | A1 | | 1/2005 | Deveney et al. |
| 2005/0033244 | A1 | | 2/2005 | Veasey et al. |
| 2005/0055011 | A1 | | 3/2005 | Enggaard |
| 2005/0205083 | A1 | | 9/2005 | Staniforth et al. |
| 2005/0268915 | A1 | | 12/2005 | Wassenaar et al. |
| 2007/0093761 | A1 | | 4/2007 | Veasey |

FOREIGN PATENT DOCUMENTS

| | | | | |
|---|---|---|---|---|
| EP | 295075 | | | 12/1988 |
| EP | 327910 | | | 8/1989 |
| EP | 327910 | | | 4/1992 |
| EP | 0 327910 | | | 4/1992 |
| EP | 0 498737 | | | 8/1992 |
| EP | 0 552 996 | A1 | * | 1/1993 |
| EP | 554996 | | | 8/1993 |
| EP | 594349 | | | 4/1994 |
| EP | 0 594349 | | | 4/1994 |
| EP | 608343 | | | 9/1994 |
| EP | 0 498 737 | | | 7/1995 |
| EP | 498737 | | | 7/1995 |
| EP | 0 702 970 | B1 | * | 9/1995 |
| EP | 702970 | | | 3/1996 |
| EP | 0 673 482 | B1 | | 4/1998 |
| EP | 879610 | | | 11/1998 |
| EP | 0 879 610 | A2 | | 11/1998 |
| EP | 937476 | | | 8/1999 |
| EP | 0 879610 | | | 8/2003 |
| EP | 0 937 476 | | | 1/2005 |
| EP | 1250167 | B1 | | 7/2005 |
| EP | 1570876 | A2 | | 7/2005 |
| FR | 2 583 291 | | | 12/1986 |
| FR | 2 767 479 | | | 2/1999 |
| JP | 3-503129 | | * | 7/1991 |
| JP | 05-337179 | A | | 12/1993 |
| JP | 06-296691 | A | | 10/1994 |
| RU | 2 111 019 | | | 5/1998 |
| WO | 89/07463 | | | 8/1989 |
| WO | WO 89/07463 | | | 8/1989 |
| WO | WO 90/09202 | | | 8/1990 |
| WO | WO 91/10460 | | | 7/1991 |
| WO | 91/14467 | | | 10/1991 |
| WO | WO 91/14467 | | | 10/1991 |
| WO | 93/07922 | | | 4/1993 |
| WO | WO 93/07922 | | | 4/1993 |
| WO | WO 96/26754 | | | 9/1996 |
| WO | 96/38190 | | | 12/1996 |
| WO | 97/36626 | | | 10/1997 |
| WO | WO 98/10813 | | | 3/1998 |
| WO | 98/10813 | | | 3/1998 |
| WO | 98/56436 | | | 12/1998 |
| WO | WO 98/56436 | | | 12/1998 |
| WO | WO 98/57688 | | | 12/1998 |
| WO | WO 99/16487 | | | 4/1999 |
| WO | WO 99/38554 | | | 8/1999 |
| WO | 99/38554 | | | 8/1999 |
| WO | 01/19434 | | | 3/2001 |

OTHER PUBLICATIONS

U.S. Appl. No. 10/960,900 File History on Feb. 8, 2008.
U.S. Appl. No. 11/121,331 File History on Feb. 8, 2008.
U.S. Appl. No. 11/640,610 File History on Feb. 8, 2008.
Decision by German Federal Patent Court Pronounced on Oct. 20, 2009, *Sanofi–Aventis Deutschland GmbH* vs. *Novo Nordisk A/S*.
Exhibit 14 in Decision by German Federal Patent Court, *Sanofi–Aventis* vs. *Novo Nordisk A/S*.
Translation of Exhibit 14 in Decision by German Federal Patent Court, *Sanofi–Aventis* vs. *Novo Nordisk A/S*.
Perspective Aug. 1999, p. 1, Innovo Secures Market Leadership; http://www.novonordisk.com/old/press/perspective/1999august/1.html.
Innovo User Manual.
May 17, 2002 Office Action in 09768760.
Declaration of Banard Sams in *Novo Nordisk A/S* v. *Sanofi–Avwentis U.S. LLC and Sanofi–Aventis*downloaded from Pacer on Feb. 29, 2008.
Complaint in *Novo Nordisk A/S*v. *Sanofi–Avwentis U.S. LLC and Sanofi–Aventis* downloaded from Pacer on Feb. 29, 2008.
Answer in *Novo Nordisk A/S*v. *Sanofi–Avwentis U.S. LLC and Sanofi–Aventis* downloaded from Pacer on Feb. 29, 2008.
File history of U.S. Appl. No. 10/610,926, which is owned by the same assignee as U.S. Appl. No. 11/122,211.
Opinion of US District Court for the District of NJ (*Novo Nordisk A/S* v. *Sanofi Aventis U.S. LLC and Sanofi Aventis,* Denying motion of a preliminary injunction, entered Feb. 20, 2008.
Hansen et al., Injection Device, a Preassembled Doses Setting and Injection Mechanism for an Injection Device, and a Method of Assembling an Injection Device, May 1, 2001.

* cited by examiner

DOSE SETTING LIMITER

Matter enclosed in heavy brackets [ ] appears in the original patent but forms no part of this reissue specification; matter printed in italics indicates the additions made by reissue.

CROSS-REFERENCE TO RELATED APPLICATIONS

This application *is a reissue of U.S. Pat. No 6,582,404, which* claims priority under 35 U.S.C. 119 of U.S. provisional application No. 60/155,612 filed on Sep. 23, 1999 and Danish application no. PA 1999 01309 filed on Sep. 16, 1999, the contents of which are fully incorporated herein by reference.

FIELD OF THE INVENTION

The present invention relates to injection devices wherein the contents of a cartridge are injected as a number of individually set doses.

Such devices have a dose setting mechanism by which the doses are set for subsequent injecting when an injection button is operated. This can be obtained by moving a carrier along a piston rod a distance proportional to the wanted dose and subsequently moving the carrier back to its original position so that the carrier carries the piston rod with it instead of being moved along said piston rod.

SCOPE OF THE RELATED ART

From EP 327 910 is known a syringe by which a dose is set by screwing a nut member up along a threaded piston rod away from a stop in a housing. The set dose is injected by pressing the end of the nut member that forms an injection button whereby the nut member is moved back to abutment with the stop again. During the latter movement of the nut member the piston rod is carried along by the nut that does not move relative to this piston rod during the injection.

When a dose is set it is convenient if a limiting device is provided which makes it impossible to set a dose that exceeds the amount of medicament which is left in the cartridge. In EP 327 910 this is obtained by the fact that the thread of the piston rod has such a length that the cartridge is just emptied when the nut is screwed to the end of the thread and then pressed home to its abutment with the stop. By setting a dose the nut can only be screwed to the end of the thread and thereby the size of the last dose is limited to comprise the remaining amount in the cartridge.

The distance the injection button has to be moved corresponds to the distance the piston in the cartridge has to be moved to inject the set dose. Especially by larger cartridges with a large cross section diameter this distance can be very short. To obtain a larger movement of the injection button a sort of gearing may be used so that the distance the injection button has to be moved is proportional with the injected dose but is a number of times the movement of the piston in the cartridge.

EP 608 343 describes an example of such a geared dose setting and injection mechanism. In this device the carrier does not cooperate directly with the threaded piston rod but with a driver element which can move the piston rod when a set dose is injected. In this device the driver element comprises a nut member which is fixed against axial displacement in the injection device. The thread of the nut member engages an outer thread of the piston rod which is secured against rotation in the injection device. By the setting of a dose the carrier is rotated away from a stop to which it is returned when the injection button is operated. During its return the carrier rotates the driver element that moves the piston rod further into the cartridge to press the piston of this cartridge so that a set amount of the medicament in the cartridge is pressed out through an injection needle at the distal end of the cartridge. As the nut member is not moved relative to the piston rod during the setting of a dose, a limiting construction as described above cannot be provided limiting the dose so it does not exceed the amount of liquid left in the injection device.

OBJECT AND SUMMARY OF THE INVENTION

An object of the invention is to provide a limiting mechanism which prevents setting of a dose that exceeds the amount of liquid left in a cartridge of an injection device of the geared type wherein a dose is set by rotating a dose setting member relative to a driver and away from a fixed stop in the injection device, and the dose is injected by rotating back the dose setting member which during this rotation carries the driver element with it to rotate this driver element which moves the piston rod forward.

Such a mechanism is according to the invention characterized in that the driver element is provided with a track having a length which is related to the total amount of medicament in the cartridge and which track is engaged by a track follower coupled to the dose setting member to follow rotation of said dose setting member. During the setting of a dose the track follower will be advanced in the track of the driver to a position depending on the set dose as during dose setting the dose setting member and the driver are rotated relative to each other. As during the injection the driver follows the rotation of the dose setting member, the pin of the dose setting member will keep its position in the track of the driver when the set dose is injected. The length of the track is so adapted that the pin reaches the end of the track and makes an increase of the set dose impossible when a dose is set which corresponds to the amount of liquid remaining in the cartridge.

According to the invention the driver may be disk shaped and have a spiral shaped track which is engaged by a cam on a member which is flexibly coupled to the dose setting member so that the pin can be moved radially when it follows the track of the driver.

In another embodiment of the invention the driver may be cylindrical and have a helical track which is engaged by a cam on the dose setting member which is a cylinder concentric with the driver.

The track may be provided as a thread in the driver and the track follower may be a nut shaped member coupled to the dose setting member and provided with a thread engaging the thread of the driver. When a dose is set the dose setting member is screwed with its thread along the thread of the driver. The limitation of the set dose is obtained by giving the threads an appropriate length.

BRIEF DESCRIPTION OF THE DRAWINGS

In the following the invention will be explained in further details with references to the drawing, wherein.

DETAILED DESCRIPTION OF THE INVENTION

Figure 1:
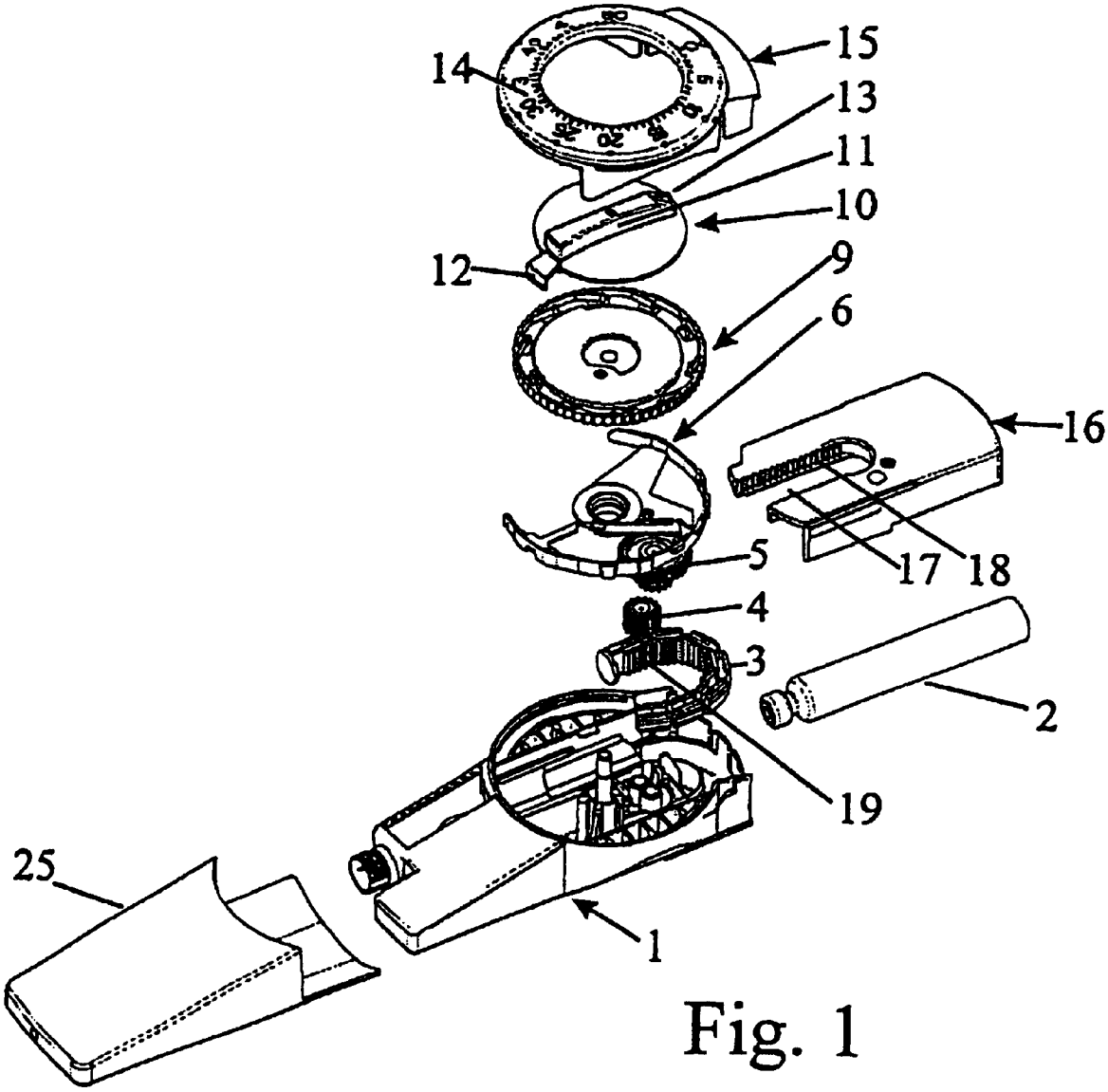
FIG. 1 shows an exploded view of a syringe with a dose limiter according to the invention.
Figure 2:
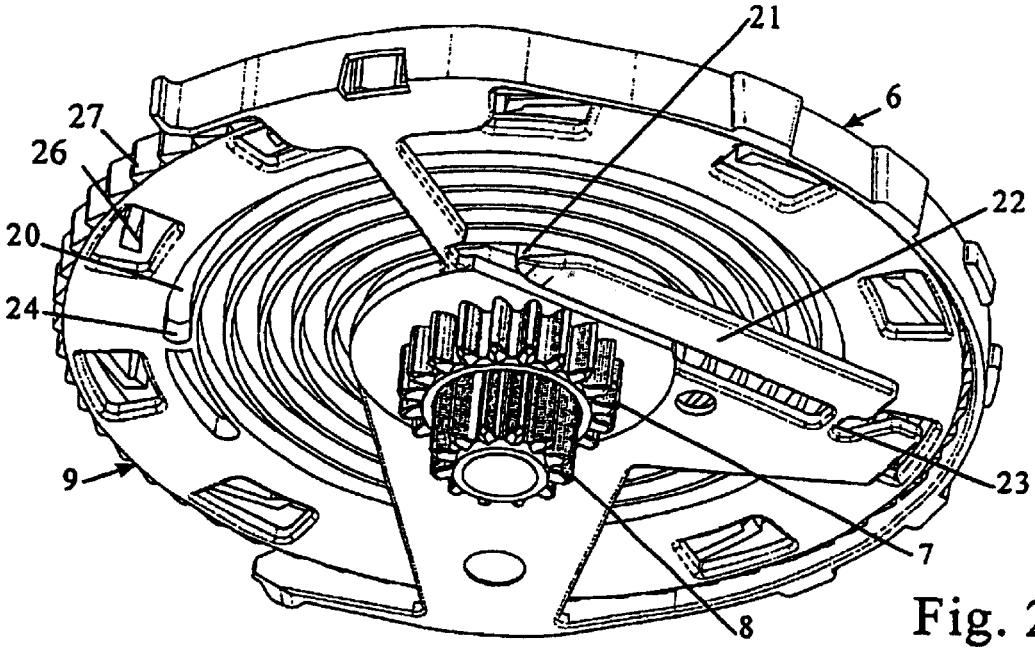
FIG. 2 shows an enlarged view of the dose setting element and the driver element of the syringe in FIG. 1.

The syringe in FIG. 1 comprises a housing 1 accommodating a cartridge 2 from which the content can be pressed out by a piston rod 3 which is by injection via gear wheels 4 and 5 advanced a distance corresponding to a dose set by dose setting. A dose setting member 6 is provided with a toothed wheel 7 surrounding a central bore through which a pinion 8 on a driver 9 projects as it is shown in FIG. 2. The dose setting element 6 is operated through an operation element 10 which has a finger grip 11, a carrier 12 which engages the dose setting member 6, and a arrow 13 pointing on a scale 14 provided on a lid 15 which forms a part of the housing 1. FIG. 1 further shows a cap 25 which can be put on to protect a not shown needle which may be mounted on the syringe, and an injection button 16 which is sliding mounted in the housing 1 and which has a recess 17 which is on one of its side surfaces provided with a cogging 18.

In the assembled syringe the toothed wheel 7 on the dose setting member 6 engages the cogging 18 of the button element 16 whereas the pinion 8 on the driver 9 engages the part with the large diameter of the gear wheel 5 the part of which with the small diameter engages the other gear wheel 4 which further engages a cogging 19 on the piston rod 3.

The driver member 9 is provided with pawl 26 which with not shown teeth in the housing forms an unidirectional coupling allowing the driver 9 to rotate only in the direction by which the piston rod 3 is advanced into the cartridge 2. A ratchet is provided by saw tooth shaped protrusions on the dose setting element 6 engaging a saw tooth cogging 27 at the perimeter of the driver 9, this ratchet being so oriented that only rotation of the dose setting member 6 in the direction in which the driver 9 can move is transmitted from the dose setting member 6 to the driver 9. By rotation of the dose setting member 6 in the opposite direction the teeth of the ratchet parts will ride over each other.

To set a dose the finger grip 11 of the operation element 10 is gripped and the element 10 is rotated clockwise until the arrow points at the wanted dose on the scale 14. As mentioned this rotation will make the ratchet parts of the dose setting element and the driver ride over each other. If the dose setting member 6 is rotated in the clockwise direction to reduce the set dose, the ratchet will cause transmission of the rotation from the dose setting member 6 to the driver 9, but the when a torque in this direction is transmitted from the operating element through the carrier 12 to the dose setting member 6, this dose setting member is deformed so that the protrusion on the dose setting member 6 is drawn out of its engagement with the toothing 27 of the driver 9 and an anticlockwise rotation of the dose setting member 6 is allowed without the rotation being transmitted to the driver 9.

Due to the engagement between the toothed wheel 7 on the dose setting member 6 and the cogging 18 of the injection button 16 this button will be lifted from the end of the housing 1 when a dose is set and will be lowered when a dose is reduced.

When the injection button 16 is pressed to inject a set dose the engagement between the toothed wheel 7 on the dose setting member 6 and the cogging 18 of the injection button 16 will cause the dose setting member 6 to rotate in an anticlockwise direction. As the torque is not transmitted to the dose setting member 6 by the operating element 10, the ratchet coupling between the dose setting member 6 and the driver 9 will be active and the driver 9 will be rotated with the dose setting member 6 in the anticlockwise direction and will drive the piston rod 3 into the cartridge.

As it is seen in FIG. 2 the disk shaped driver 9 has in its side facing the dose setting member 6 a spiral shaped track 20 which is engaged by a cam 21 provided at the end of an arm 22 which is by a flexible beam 23 fastened to the dose setting member 6 so that the arm 22 can swing to let the cam 21 move in the radial direction of the driver 9. When the dose setting member 6 during the setting of a dose is rotated relative to the driver 9 the cam is moved along the track 20 whereas the cam during the injection due to the concomitant rotation of the dose setting member 6 and the driver 9 remains in its position in the track 20 obtained during the dose setting. This way the position of the cam in the track reflects the total amount of medicine administered. When the cam 21 abuts the end wall 24 of the track 20 the set dose cannot be increased and by adapting the length of the track to the total amount of medicine in the cartridge it is ensured that a dose larger than the amount of medicine remaining in the cartridge cannot be set.

Figure 3:
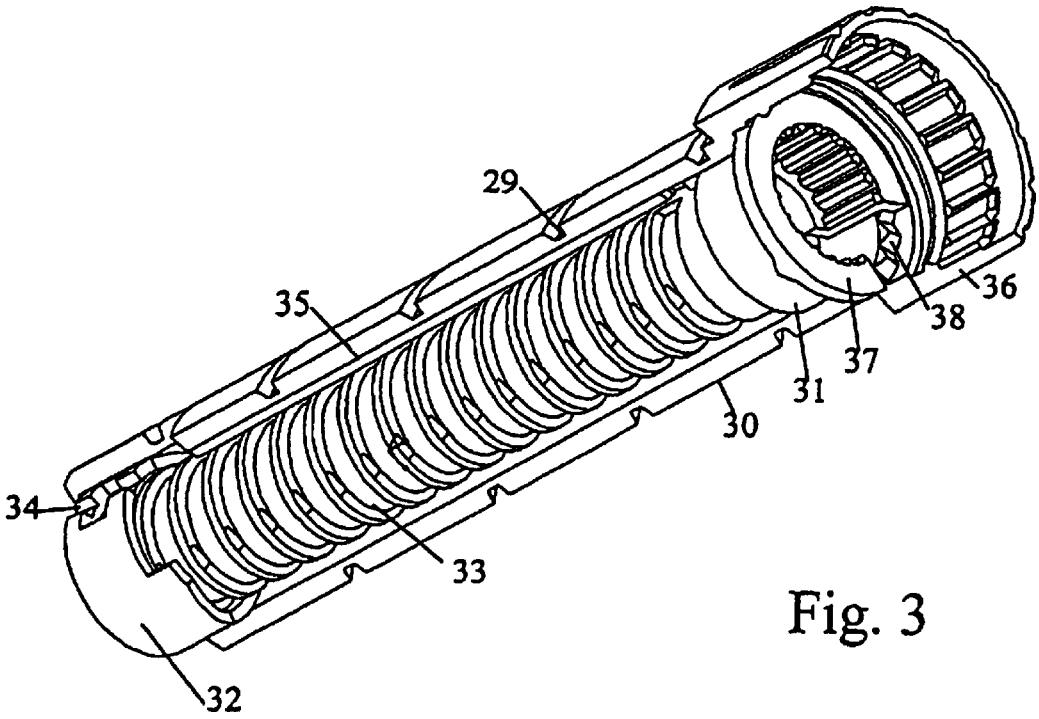
FIG. 3 shows the dose setting member, the driver, and the track follower of another embodiment of an injection syringe.

FIG. 3 shows a dose setting member 30 surrounding a driver 31 of another embodiment of a dose setting limiter. The dose setting member 30 is cylindrical and is on its outer wall provided with a helical track 29 which is designed to co-operate with a helical inner ridge in a not shown housing so that the dose setting member 30 is screwed outward in said housing when rotated to set a dose and inward in said housing when rotated to reduce a too large set dose. During the dose setting rotation the dose setting member 30 is rotated freely relative to the driver 31 which it surrounds. Between the dose setting member 30 and the driver 31 a nut member 32 is coupled which can when it is rotated relative to the driver 31 be screwed up along this driver which is at its outer surface provided with a helical track 33. At its outer wall the nut member 32 is in the axial direction provided with a recess 34 which is engaged by a ridge 35 in the axial direction on the inner side of the dose setting element 30.

During the setting of a dose the nut member 32 is due to the engagement between the ridge 35 and the recess 34 rotated with the dose setting member 30 relative to the driver 31 so that the position of the nut member 32 on this driver is dependent on the dose set. When the dose is injected by pressing a not shown injection button which is placed in an end part 36 of the dose setting member 30 this button presses a flange 37 at an end of the driver 31 into engagement with coupling teeth 38 at the bottom of the end part 36 of the dose setting member 30. On its lower not visible side the flange 37 is provided with coupling teeth corresponding to the coupling teeth 38 of the dose setting member 30 and when the dose setting member 30 is due to the engagement between the track 29 in the dose setting member 30 and the ridge in the housing forced to rotate relative to the housing when it is pressed into the housing the rotation will be transmitted to the driver 31 which due to the engaging coupling teeth is forced to rotated with the dose setting member and during this rotation the nut member 32 will maintain its position on the driver 31. This way the position of the nut member 32 on the driver 31 will always indicate the total sum of set and injected doses. When the length of the helical track 33 in the driver 31 is adapted to the amount of medicine in a cartridge the nut member 32 will reach the end of the track 33 and stop for setting a dose larger than the amount remaining in the cartridge.

What is claimed is:

1. A limiting mechanism that prevents setting of a dose that exceeds the *injectable* amount of liquid left in a cartridge of an injection device wherein a dose is set by rotating a dose setting member relative to a driver and away from a fixed stop in the injection device, and the dose is injected by [rotating] *pressing an injection button which rotates* back the dose setting member which during this rotation carries the driver with it to rotate this driver which moves the piston rod forward, wherein the driver is provided with a track having a length which is related to the total *injectable* amount of medicament in the cartridge and which track is engaged by a track follower coupled to the dose setting member to follow rotation of this dose setting member and wherein the driver is disk shaped and the track has a spiral shape which is engaged by the track follower which is flexibly coupled to the dose setting member so that the track follower can be moved radially when it follows the track of the driver element.

2. A limiting mechanism that prevents setting of a dose that exceeds the amount of liquid left in a cartridge of an injection device wherein a dose is set by rotating a dose setting member relative to a driver and away from a fixed stop in the injection device, and the dose is injected by rotating back the dose setting member which during this rotation carries the driver with it to rotate this driver which moves the piston rod forward, wherein the driver is provided with a track having a length which is related to the total amount of medicament in the cartridge and which track is engaged by a track follower coupled to the dose setting member to follow rotation of this dose setting member and wherein the driver is cylindrical and the track has a helical shape which is engaged by the track follower which is coupled to the dose setting member so that the track follower can be moved rotationally when it follows the track of the driver element.

3. The limiting mechanism of claim 2, wherein the dose setting element is a cylinder concentric with the driver.

4. The limiting mechanism of claim 3, wherein the track comprises a thread in the driver and that the track follower comprises a nut shaped member coupled to the dose setting member and provided with a thread engaging the thread of the driver.

*5. A dose setting limiter assembly that prevents the setting of a dose which exceeds the remaining injectable amount of medication in a multiple dose cartridge in an injection device which comprises: a cylindrical dose setting member having an outer wall provided with a helical groove which allows the cylindrical dose setting member to be screwed out of the injection device and away from an initial position when the cylindrical dose setting member is rotated during dose setting and screwed into the device and toward the initial position to reduce the size of a set dose, wherein during injection of the set dose the cylindrical dose setting member is pressed back into the device and as a result of the helical groove it rotates back toward the initial position;*

*wherein the dose setting limiter assembly comprises:*

*(a) a helical track disposed on the outer surface of a hollow cylindrical driver that drives a separate piston rod forward; and*

*(b) a follower that engages the helical track;*

*wherein the follower moves along the helical track when the dose setting member is rotated during dose setting; but wherein the follower does not move along the track during injection of the set dose; wherein the injection of the set dose is carried out by pressing an injection button which:*

*(i) presses the cylindrical dose setting member back into the device, and*

*(ii) causes the cylindrical dose setting member to rotate back to the initial position, wherein the rotation back is cause by the helical groove on the dose setting member;*

*wherein the position of the follower along the track is indicative of the total sum of the set and injected doses;*

*wherein the length of the helical track that the follower can move along corresponds to the amount of medication in the cartridge that is available to be injected; and*

*wherein the follower abuts a stop at the end of the track during dose setting before the cylindrical dose setting element can be rotated to dial up a dose that would exceed the injectable amount of medication remaining in the cartridge.*

*6. The dose setting limiter assembly of claim 5, wherein when the follower abuts the stop at the end of the track during dialing up of a dose, the cylindrical dose setting member cannot be rotated further to increase the size of the dose.*

*7. The dose limiter assembly of claim 6, wherein the follower is a nut like element and the helical track is a thread and wherein the follower engages the thread.*

*8. The dose limiter assembly of claim 7, wherein the driver, the helical grove, the helical track, and the dose setting member are oriented so that they are all coaxial.*

*9. A dose limiter mechanism for use with in an injection device, which comprises:*

*(i) a rotatable hollow cylindrical dose setting member containing a threaded groove on its outer surface so that it screws out of the injection device during setting of a dose when it is rotated, screws back into the housing to reduce the size of a set dose when it is rotated back, and screws back into the housing when an injection button is pressed during injection, and*

*(ii) a hollow cylindrical piston rod driver that is coaxial with the hollow cylindrical dose setting member;*

*wherein the dose limiting mechanism operates within the injection device to prevent the setting of a dose that exceeds the injectable amount of medication remaining in a multiple dose cartridge in the device; and wherein the dose limiter mechanism comprises:*

*a helical track disposed on the outer surface of the piston rod driver, the helical track having a length that corresponds to the injectable amount of medication in the cartridge; a follower that engages the helical track and moves along the helical track when the dose setting member is rotated during dose setting but that remains in a fixed position on the helical track when the dose setting member is rotated back when the injection button is pressed during injecting of medication, and wherein the distance the follower moves during dose setting corresponds to the size of the set dose and wherein the follower abuts a stop at the end of the helical track when an attempt is made to rotate the dose setting member during dose setting that would result in a dose being set that exceeds the remaining injectable amount of medication in the cartridge.*

*10. The mechanism of claim 9, wherein the hollow cylindrical dose setting member is prevented from rotating to increase the size of a set dose when the follower hits the stop.*

*11. The mechanism of claim 9, wherein the track on the hollow cylindrical piston rod driver forms a thread and follower comprises a nut like element that threadly engages the thread.*

*12. The mechanism of claim 10, wherein the track on the hollow cylindrical piston rod driver forms a thread and the follower comprises a nut like element that threadly engages the thread.*

*13. An injection device dose limiter assembly for use with both*

*(a) a rotatable cylindrical dose setting member, which threadly engages an injection device housing element*

*so that (i) when it is rotated to set the size of a dose it screws out of an injection device housing, (ii) when it is rotated back to reduce the size of a set dose it screws back into the housing, and (iii) when an injection button is pressed during injecting of medication the cylindrical dose setting member is pressed back into the housing and rotates back, and*

*(b) a hollow cylindrical piston rod driver that drives a separate piston rod during injection of the set dose;*

*wherein the injection device dose limiter prevents the setting of a dose that is larger than the injectable amount of medication remaining in a multi dose cartridge and*

*wherein the injection device dose limiter assembly comprises:*

*a helical track disposed on the outside of the hollow cylindrical piston rod driver; and*

*a follower that moves along the track during dose setting but remains stationary with respect to the helical track during dose injecting when an injection button is pressed which causes the cylindrical dose setting member to be screwed back into the housing; wherein the length of the track that the follower is capable of moving along corresponds to the injectable amount of medication in an injection device multiple dose cartridge; and*

*wherein during dose setting:*

*the follower moves a distance along the track that corresponds to the size of the dose being set; and*

*wherein the follower abuts a stop before the size of the set dose exceeds the injectable amount of medication remaining in the cartridge.*

*14. The assembly of claims 5 or 13, wherein the follower abuts the stop when the size of the set dose equals the injectable amount of medication remaining in the cartridge.*

*15. The assembly of claims 5 or 13, wherein the helical track has a length adapted to ensure that the follower stops advancing when the size of a set dose is equal to that remaining for injection.*

*16. The assembly of claims 1, 5, or 13, wherein the injection button moves a distance proportional to, but a number of times greater than, the distance a piston in the cartridge moves during delivery of the set dose during dose injecting.*

*17. The mechanism of claim 9, wherein the follower abuts the stop when the size of the set dose equals the injectable amount of medication remaining in the cartridge.*

*18. The mechanism of claim 9, wherein the helical track has a length adapted to ensure that the follower stops advancing when the size of a set dose is equal to that remaining for injection.*

*19. The mechanism of claim 9, wherein the injection button moves a distance proportional to, but a number of times greater than, the distance a piston in the cartridge moves during delivery of the set dose during dose injecting.*

* * * * *